United States Patent [19]
Sarvazjan et al.

[11] Patent Number: 5,509,299
[45] Date of Patent: Apr. 23, 1996

[54] APPARATUS FOR DETERMINING PHYSICAL PROPERTIES OF FLUIDS

[75] Inventors: Armen P. Sarvazjan, Puschino; Vladimir N. Belonenko, Razvilka, both of Russian Federation

[73] Assignee: Aktsionernoe Obschestvo Zakrytogo Tipa "Biotekhinvest", Moscow, Russian Federation

[21] Appl. No.: 211,684

[22] PCT Filed: Aug. 12, 1993

[86] PCT No.: PCT/RU93/00200

§ 371 Date: Sep. 6, 1994

§ 102(e) Date: Sep. 6, 1994

[87] PCT Pub. No.: WO94/04914

PCT Pub. Date: Mar. 3, 1994

[30] Foreign Application Priority Data

Aug. 13, 1992 [RU] Russian Federation ............... 5058556

[51] Int. Cl.⁶ ................................................. G01N 29/00
[52] U.S. Cl. .................. 73/64.53; 73/61.79; 310/322; 310/348
[58] Field of Search ............................... 73/61.45, 64.53, 73/61.49, 61.79, 53.01, 597; 310/322, 348

[56] References Cited

U.S. PATENT DOCUMENTS

| | | | |
|---|---|---|---|
| 2,711,646 | 6/1955 | Mendousse | 73/64.53 |
| 2,833,142 | 5/1958 | Runquist et al. | 73/64.53 |
| 4,098,128 | 7/1978 | Baumert | 73/591 |
| 4,249,422 | 2/1981 | Gaunaurd et al. | 73/589 |
| 4,325,255 | 4/1982 | Howard et al. | 73/589 |
| 4,936,143 | 6/1990 | Schutten et al. | 73/597 |
| 4,969,362 | 11/1990 | Zacharias et al. | 73/61.79 X |

FOREIGN PATENT DOCUMENTS 1226279 4/1986 U.S.S.R. .
1226279A 4/1986 U.S.S.R. .

OTHER PUBLICATIONS

Tribological problems: V. N. Beloneko (Ultrasonics 1991 vol. 29 Mar. pp. 107–118.
"Role of Bulk Viscosity . . . ", V. N. Beloneko (Ultrasonics 1991, vol. 29, Mar. pp. 101–106.
"Development of Methods of Precise Ultrasonic Measurements . . . " A. P. Sarvazyan (Ultrasonics Jul. 1982) pp. 151–154.
Translation entitled, "Interferometers", 1988 translation of portion of: "Der Ultraschall Und Seine Anwendung in Wissenschaft und Technik" von Dr. Ludwig Bergmann, Zürich, 1954.
Role of Bulk Viscosity and Acoustic Parameters In Tribological Problems—Ultrasonics, vol. 29, Mar. 1991, pp. 101 & 108.

*Primary Examiner*—Hezron E. Williams
*Assistant Examiner*—Michael J. Brock
*Attorney, Agent, or Firm*—Keck, Mahin & Cate

[57] ABSTRACT

The invention relates to instruments for precision measurements at different pressures and temperatures of the physical properties of fluids such as isothermal and adiabatic compressibility, density, coefficient of thermal expansion, velocity and absorption of ultrasound; for determining on their base the heat capacities, other thermophysical and thermodynamic properties, functions and potentials. The apparatus comprise a casing (1), made as a pressure vessel with a measuring chamber, a piston (8), a unit (14) for excitation and reception of signals, recording and processing of data, an oscillation transducer (5) installed in the chamber and forming two measuring intercommunicating cells with a constant (6) and a variable (7) path respectively. A piston insert (17) may be installed with a slide fit between the piston and the oscillation transducer. The apparatus ensures a higher accuracy and resolving power of measurements of physical properties of fluids under various pressures, volumes and temperatures.

12 Claims, 2 Drawing Sheets

APPARATUS FOR DETERMINING PHYSICAL PROPERTIES OF FLUIDS

FIELD OF ART

The present invention relates to instrument engineering and can be utilized for precision measurements of physical properties of fluids at high pressures in oil and gas industries, mechanical engineering, medicine, biology, ect.

PRIOR ART

Known in the prior art is a high-pressure apparatus (V. N. Belonenko "Ultrasonics" 1991, vol 29, March, p. 108) comprising an acoustic chamber with a variable base and a press with a piston combined in a single hydraulic unit. Connecting the piston with a displacement indicator permits determining the distance covered by the piston, the changes in the volume of test fluid under pressure, its density and isothermal compressibility. Said apparatus is deficient in its low accuracy of determination of said characteristics.

The closest apparatus in its essence to the claimed one is the apparatus for testing the parameters of fluids (USSR Invertor's Certificate No. 1,226,279, G OI N 29/02, 1986). Said apparatus comprises a high-pressure chamber with a piston, and ultrasonic piezotransducers disposed outside of the casing, a load unit, a displacement meter, and an electronic unit for excitation of pulse signals, their reception, processing and recording of data.

A disadvantage of said apparatus lies in a low accuracy of determining acoustic parameters, density and compressibility.

An essential disadvantage of the above-quoted apparatuses is a low accuracy in determining the coefficient of isothermal compressibility. This reduces radically the efficiency of acoustic methods and prevents their reliable use for determining the thermophysical properties of fluids, such as isobaric $C_p$ and isochoric $C_v$ heat capacities, since the relation $C_p/C_v = \beta_T/\beta_S$ where $\beta_T$—coefficient of isothermal compressibility, $\beta_S = 1/\rho.c^2$—coefficient of adiabatic compressibility, $\rho$—density, and c—sound velocity. With highly accurate determination of the ultrasound velocity, the accuracy of determining the coefficient of compressibility and heat capacities depends on the accuracy of determining the density and volume and their changes under the effect of pressure and temperature.

DISCLOSURE OF THE INVENTION

The main object of the invention resides in raising the accuracy and resolving power when measuring the physical properties of fluids under varying PVT (P—pressure, V—volume, T—temperature).

This object is attained by providing an apparatus comprising a chamber with fluid, a piston, a casing, a thermostat, an oscillation transducer and a unit for excitation and reception of signals, recording and processing of data wherein the oscillation transducer is accommodated inside the chamber parallel to the end surface of the piston so as to form two measuring cells, having constant and variable acoustic paths, respectively.

Radiation of the piezocrystal into the cell with a permanent acoustic base provides for measuring the velocity and absorption of sound while its radiation into the variable acoustic path cell gives a notion of piston displacement. The distance covered by the piston is found either by the signal transmission time or by the wavelength and frequency and/or by counting the number of half-waves that fit into the distance between the crystal and the reflecting surface of the piston. Such an arrangement of the oscillation transducer makes it possible by the use of the piston to combine the pressure-producing function with precision measurement of piston travel and change of volume; density; isothermal compressibility; velocity and absorption of ultrasound; determining isobaric and isochoric heat capacities; coefficient of thermal expansion and other thermophysical properties, thermodynamic functions and potentials, etc. Besides, the piston is used to compensate for changes of volume under various PVT conditions.

The concurrent use of the constant acoustic path and variable acoustic path cells also broadens substantially the capabilities of the apparatus in measuring the sound attenuation coefficient. In this case excitation of continous oscillations and making measurements in the resonant mode allows determining displacement and, therefore, isothermal compressibility by measuring the oscillation frequency, thereby ensuring a higher accuracy.

Making the measuring chamber with a volume which is by far larger than its changes enhances stability of readings and accuracy of determining the values concerned with the changes of volume, density, compressibility, coefficient of thermal expansion, etc. because accuracy of their determination also depends on the relation of volumes of variable acoutic path and constant acoustic path cells, the relation $\Delta V/V$, $\Delta f/f$ accuracy of volume measurement, and oscillation frequency where V and $\Delta V$—volume and its change, f and $\Delta f$—frequency and its change in the variable accoustic base. These characteristics of the apparatus make it also suitable for other applications, for example in the capacity of a precision temperature meter.

However, it is expedient that the volume of the chamber be selected on the basis of its optimum value which depends on the required accuracy of the parameters being measured. An excessively large volume complicates the pressure-producing and maintaining systems, and increases the size and metal content of the apparatus.

Putting the cells in communication with each other creates identical conditions therein, simplifies the apparatus and promotes its reliability.

Provision of the piston whose diameter is larger than that of the oscillation transducer surface which radiates towards the piston reduces diffraction distortions of the signal.

A piston insert assembled with a slide fit in the channel between the piston and the oscillation transducer increases the reliability of sealing the apparatus due to a tight contact between insert and channel surfaces and the possibility of additional sealing of the piston because the insert performs the function of reflector and because the mounting requirements for the piston are substantially simplified.

This expands the capabilities of the apparatus for the tests conducted in a wider range of pressure and temperature variations. Said arrangement of the insert also increases the accuracy of measurements since it guarantees the parallelism of the insert reflecting surface and the radiating surface of the oscillation transducer. This is difficult to achieve by means of the reflecting surface of the sealed piston since said surface will inevitably deviate from the required position under the influence of seals (or glands).

Bending the opposite end of the piston insert into the insert body seal s off the measuring chamber additionally so that in case of a pressure rise this practically rules out the influence of other reflected waves except the main one.

Filling the space between the piston and the insert with a fluid whose modulus of elasticity is higher than that of the test fluid makes transmission of pressure into the measuring chamber with the aid of the main piston more effective. If the selected fluids are immiscible, the probability of their penetration into the gap between the insert and the casing surface is reduced.

The casing of the apparatus or the member thereof is made so that it forms, together with the piston, a plunger-and-barrel pair thereby promoting the accuracy of measurements and the reliability of the apparatus. Sealing of the piston also pursues the same purpose, simultaneously extending the range of built-up pressures.

BRIEF DESCRIPTION OF THE DRAWINGS

The design of the apparatus is elucidated by the following drawings.

BEST MODE OF CARRYING OUT THE INVENTION

Figure 1:
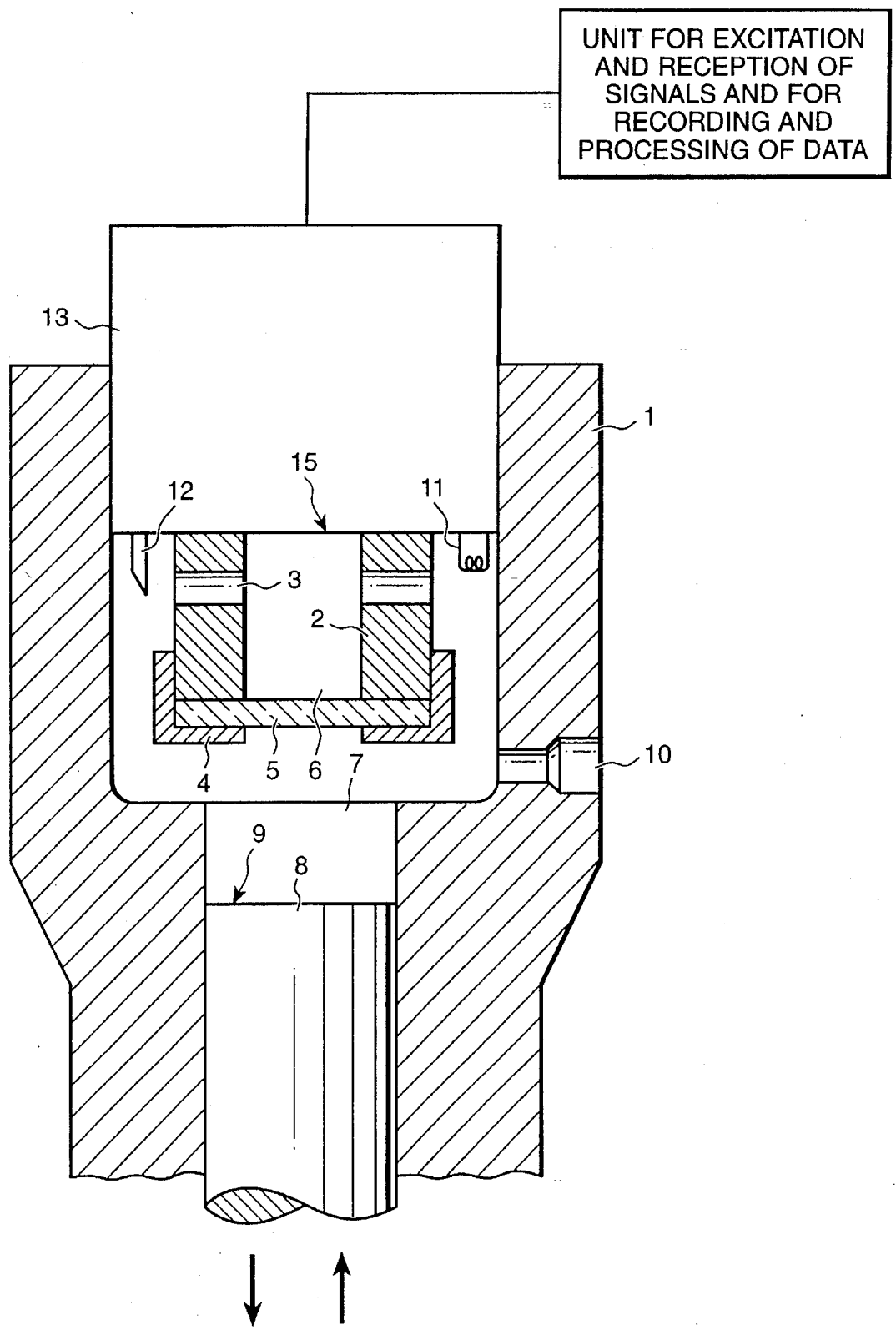
FIG. 1 is a schematic diagram of the apparatus.

The apparatus comprises a casing 1 in the form of a high-pressure vessel wherein installed on a holder 2 with holes 3 by means of a fastener 4 is an oscillation transducer 5 (in this case a piezocrystal of lithium niobate, cut Y-36) arranged so form two measuring cell s with constant 6 and variable 7 acoustic paths. Pressure is built up in the measuring cells by a piston 8 with a surface 9 reflecting ultrasonic waves, said piston conjugated with the member of the casing 1 wherein it moves in the manner of a plunger-and-barrel pair. The measuring chamber is filled with fluid through a hole 21. The chamber is provided with a pressure sensor 11 (e.g. manganin pressure gauge) and a temperature gauge 12 (e.g. thermocouple), both being connected by electric inputs (not shown) in cover 13 with an electronic unit for excitation and reception of signals, recording and processing of data. Electrodes (not shown) sprayed onto the surface of the piezocrystal 5 are connected to the unit also by electric inputs. The cover 13 has a reflecting surface 15 which is parallel with the radiating surface of the piezocrystal 5.

The measuring cells 6 and 7 may be filled either with one and the same test fluid, or with the test and, for example, reference fluid. In this case pressure is transmitted from the cell 7 into the cell 6, for example, through a flexible member (now shown) which covers the holes 3 and separates the fluids. In this case there is no need for installing sensors 11 and 12 since the cell 6 can function as a pressure or temperature meter.

For taking measurements at varying temperatures and under different thermodynamic conditions, the apparatus is placed into a thermostatic jacket (not shown).

The invention is illustrated by the following examples.

Figure 2:
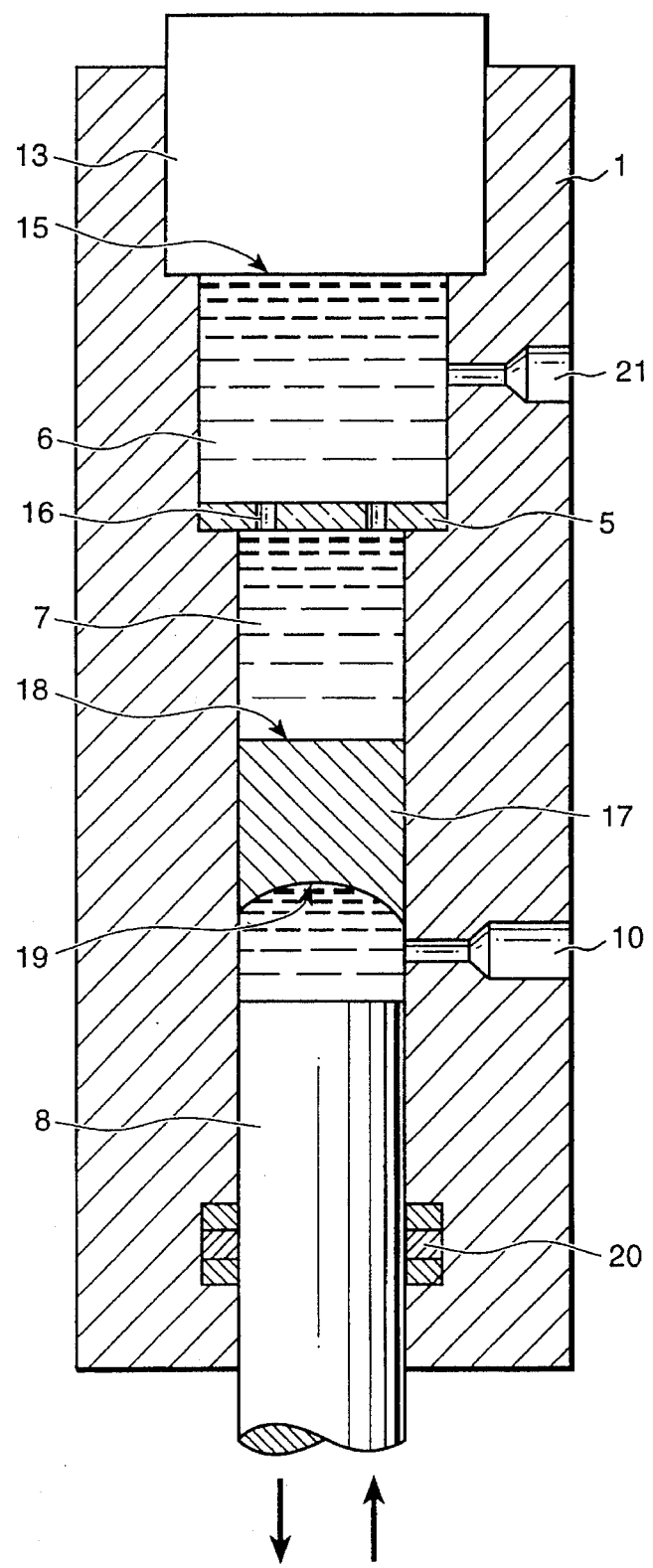
FIG. 2 shows the design of the apparatus with a piston insert.

EXAMPLE 1. Shown in FIG. 2 is another embodiment of the apparatus wherein the piezocrystal 5 divides the measuring chamber into the cell 6 with a constant acoustic path and the cell 7 with a variable acoustic path. The cells communicate with each other through holes 16 in the crystal. Disposed between the piston 8 and the piezocrystal 5 is a piston insert 17 with a reflecting surface 18 and a concave surface 19. A seal 20 provides for better pressure tightness and a wider range of pressures.

EXAMPLE 2. The apparatus may be made with additional oscillation transducers (not shown) instead of the reflecting surface 15 on the cover 13 and/or 9 on the piston 8. Such an arrangement of transducers complicates the design somewhat, but simultaneously widening the capabilities of the apparatus, permitting the use of various measuring circuits, facilitating the discrimination of the signal that has passed through the fluid. Similarly to the prototype, the additional transducers may be brought outside of the casing. In this case the dimensions of the cover and piston should be calculated as acoustic delays or they should be provided with acoustic lines in the capacity of acoustic delays.

The measurements are made as follows.

The volume of the apparatus to be filled with fluid is calculated by conventional methods. The measuring chamber is vacuumized through the hole 10. The apparatus and the burette (not shown) with the test fluid, in this example gas condensate, are thermostated at room (or preset) temperature.

The density of condensate is determined at the same temperature by conventional methods, e.g. by hydrostatic weighing. Then the cells 6,7 are filled with gas condensate, the hole 10 is closed with a plug (not shown) and the measuring temperature is created and maintained by a thermostat. A sinusoidal signal is delivered to the piezocrystal 5. Measurements of resonant frequency, quality, velocity and absorption of ultrasound are made in the constant path cell using the conventional methods for the constant path interferometer. Moving the piston, pressure is increased in both cells and acoustic characteristics are measured depending on pressure at constant temperature. Changes in the frequency of oscillations during movement of the piston are used for determining the amount of its travel and changes in the volume and density, while pressure in the cells is measured with the aid of the sensor 11.

The coefficient of isothermal compressibility is found from expression:

$$\beta_T = -\frac{1}{V}\left(\frac{\partial V}{\partial P}\right)_T = k\left(\frac{\partial f_{res.}}{\partial P}\right)_T$$

where V—volume, T—temperature, P—pressure, $f_{res.}$ resonant frequency, k—proportionality factor.

The relation of resonant frequencies of the resonator cell with a variable acoustic path to the resonant frequencies of the resonator cell with a constant path allows also compensating the effect of temperature distortions on the results.

The density can be found from the expression:

$$\frac{\rho_P}{\rho_o} = \frac{V_o}{V_P}$$

where $\rho_o$, $V_o$—density and volume at atmospheric pressure, respectively, $\rho_p$ and $V_p$ density and volume at pressure P.

If one knows, apart from the traditional acoustic parameters, the isothermal compressibility and density, the complex of thermodynamic, thermophysical, molecular-kinetic and physicochemical properties, functions and potentials, etc. is calculated with the help of conventional methods. The physical principles built into the apparatus allow a similar design to be used for analogous purposes also with other types of oscillation sources (transducers) of, say, electromagnetic and SHF (microwave) oscillations.

INDUSTRIAL APPLICABILITY

The present invention can be used to the best advantage for precision measurements of the physical properties of fluids in oil and gas industries, mechanical engineering, also in medicine and biology. The apparatus broadens substantially the possibilities of acoustic methods since it permits determining with a high precision not only the traditional acoustic parameters but also thermophysical properties determined heretofore mainly by calorimetric methods.

Those skilled in the art will also visualize the other possibilities and advantages of the claimed apparatus.

We claim:

1. An apparatus for determining the physical properties of fluids comprising a casing with a measuring chamber inside, a piston, an oscillation transducer, a unit for excitation and reception of signals and for recording and processing of data, wherein the transducer is installed inside the chamber parallel with an end surface of the piston so that it divides the chamber into two measuring cells with constant and variable acoustic paths, respectively.

2. The apparatus of claim 1, wherein a volume of the constant path cell is larger than that of the variable path cell.

3. The apparatus of claim 1, wherein a total volume of the measuring chamber is larger than that of a changing part of its volume.

4. The apparatus of claim 1, wherein the measuring cells with constant and variable paths are resonators.

5. The apparatus of claim 1, wherein the cells with constant and variable paths are in communication with each other.

6. The apparatus of claim 1, wherein the oscillation transducer is made of a piezocrystal.

7. The apparatus of claim 1, comprising a piston insert having a reflecting end surface directed towards the oscillation transducer and disposed with a slide fit between the piston and the oscillation transducer.

8. The apparatus of claim 7, wherein the end surface of the piston insert directed away from the oscillation transducer has a concave surface.

9. The apparatus of claim 1, wherein a space between the piston and a piston insert contains a further fluid with a lower compressibility than a test fluid.

10. The apparatus of claim 1, wherein a space between the piston and a piston insert contains a fluid immiscible with a test fluid.

11. The apparatus of claim 1, wherein the piston and the casing in which the piston moves are made as a plunger-and-barrel pair.

12. The apparatus of claim 1, wherein the piston is sealed.

\* \* \* \* \*